United States Patent
Osbrink

(10) Patent No.: US 9,833,597 B2
(45) Date of Patent: Dec. 5, 2017

(54) TEXTILE BALLOON CATHETERS

(71) Applicant: Cook Medical Technologies LLC, Bloomington, IN (US)

(72) Inventor: Ruth Osbrink, Bloomington, IN (US)

(73) Assignee: COOK MEDICAL TECHNOLOGIES LLC, Bloomington, IN (US)

( * ) Notice: Subject to any disclaimer, the term of this patent is extended or adjusted under 35 U.S.C. 154(b) by 287 days.

(21) Appl. No.: 14/708,327

(22) Filed: May 11, 2015

(65) Prior Publication Data

US 2015/0320986 A1  Nov. 12, 2015

Related U.S. Application Data

(60) Provisional application No. 61/991,769, filed on May 12, 2014.

(51) Int. Cl.
*A61M 25/10* (2013.01)
*D03D 3/02* (2006.01)
(Continued)

(52) U.S. Cl.
CPC .......... *A61M 25/10* (2013.01); *A61M 25/104* (2013.01); *A61M 25/1027* (2013.01); *A61M 25/1029* (2013.01); *A61M 25/1034* (2013.01); *D03D 1/00* (2013.01); *D03D 3/02* (2013.01); *D03D 13/00* (2013.01); *A61M 2025/1084* (2013.01); *D10B 2509/00* (2013.01); *Y10T 29/49828* (2015.01); *Y10T 156/10* (2015.01)

(58) Field of Classification Search
CPC .................. A61M 25/1027; A61M 2025/1031
See application file for complete search history.

(56) References Cited

U.S. PATENT DOCUMENTS 4,487,567 A   12/1984 Possis et al.
4,816,028 A   3/1989 Kapadia et al.
(Continued)

FOREIGN PATENT DOCUMENTS

WO   WO9940875   8/1999

OTHER PUBLICATIONS

Snijder, et al., "Customization Is Key: How Biomedical Textiles Using High-Performance Medical-Grade Fiber Can Deliver Improved Device Performance," Biomedical Structures, DSM, Jun. 2011, pp. 1-6.

(Continued)

*Primary Examiner* — Jeff Aftergut
(74) *Attorney, Agent, or Firm* — Buchanan Van Tuinen LLC

(57) ABSTRACT

Textile balloon catheters, textile sleeves useful in balloon catheters, and methods of making balloon catheters are described. An example catheter includes an elongate shaft and a balloon movable between uninflated and inflated configurations, and a textile sleeve secured to the balloon. The textile sleeve has a plurality of warp threads and at least one weft thread extending circumferentially around the balloon. Circumferential loops in the portion of the textile sleeve that is secured to the body of the balloon are larger in diameter than circumferential loops in the portion of the textile sleeve that is secured to one or more of the proximal neck, distal neck, proximal cone and distal cone portions of the balloon.

16 Claims, 8 Drawing Sheets

(51) Int. Cl.
*D03D 1/00* (2006.01)
*D03D 13/00* (2006.01)

(56) References Cited

U.S. PATENT DOCUMENTS

| | | | |
|---|---|---|---|
| 4,892,539 A | 1/1990 | Koch | |
| 5,279,539 A | 1/1994 | Bohan et al. | |
| 5,496,364 A | 3/1996 | Schmitt | |
| 5,509,931 A | 4/1996 | Schmitt | |
| 6,485,515 B2 | 11/2002 | Strecker | |
| 6,592,614 B2 | 7/2003 | Lenker et al. | |
| 6,729,356 B1 * | 5/2004 | Baker | A61B 17/12022 139/383 AA |
| 6,814,753 B2 | 11/2004 | Schmitt | |
| 8,382,927 B1 * | 2/2013 | Tayebi | A61M 25/1029 156/148 |
| 8,470,013 B2 | 6/2013 | Duggal et al. | |
| 8,715,229 B2 * | 5/2014 | Davies, Jr. | A61M 25/1029 604/103 |
| 8,881,365 B2 | 11/2014 | Kuppurathanam et al. | |
| 9,095,462 B1 * | 8/2015 | Tayebi | A61F 2/958 |
| 9,126,022 B2 | 9/2015 | Kuppurathanam | |
| 9,174,030 B2 | 11/2015 | Boatman | |
| 9,192,747 B2 | 11/2015 | Hardert | |
| 2008/0183132 A1 * | 7/2008 | Davies | A61M 25/104 604/103.09 |
| 2009/0171443 A1 | 7/2009 | Kuppurathanam et al. | |
| 2011/0046654 A1 | 2/2011 | Kuppurathanam | |
| 2012/0277783 A1 * | 11/2012 | Cummins | A61M 25/104 606/191 |
| 2013/0261547 A1 | 10/2013 | Aggerholm et al. | |
| 2015/0297871 A1 | 10/2015 | Aggerholm et al. | |
| 2015/0352336 A1 | 12/2015 | Kuppurathanam | |

OTHER PUBLICATIONS

European Patent Office, Extended European Search Report, for European Application No. 15167413.2, issued Dec. 22, 2015, pp. 1-5.

* cited by examiner

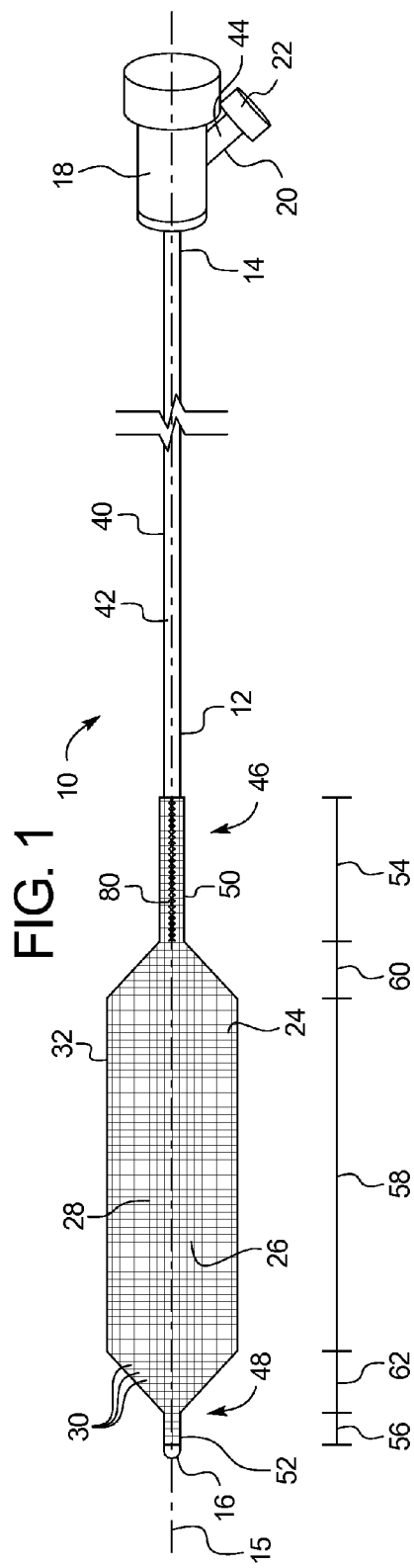

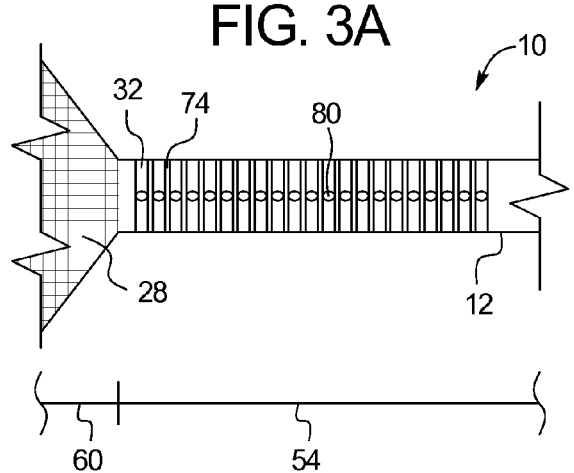
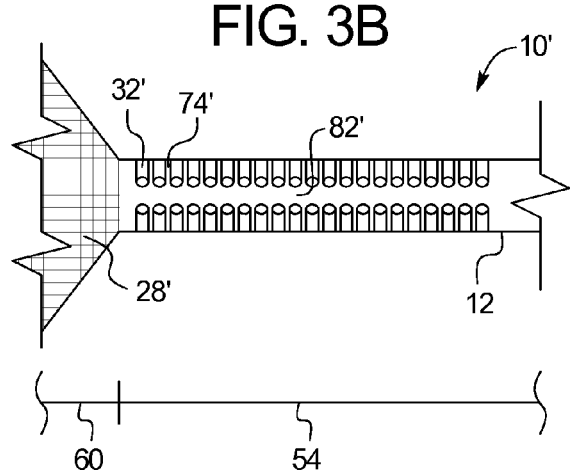
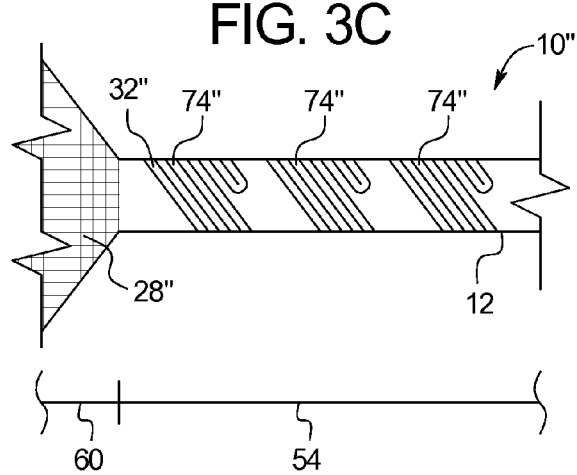

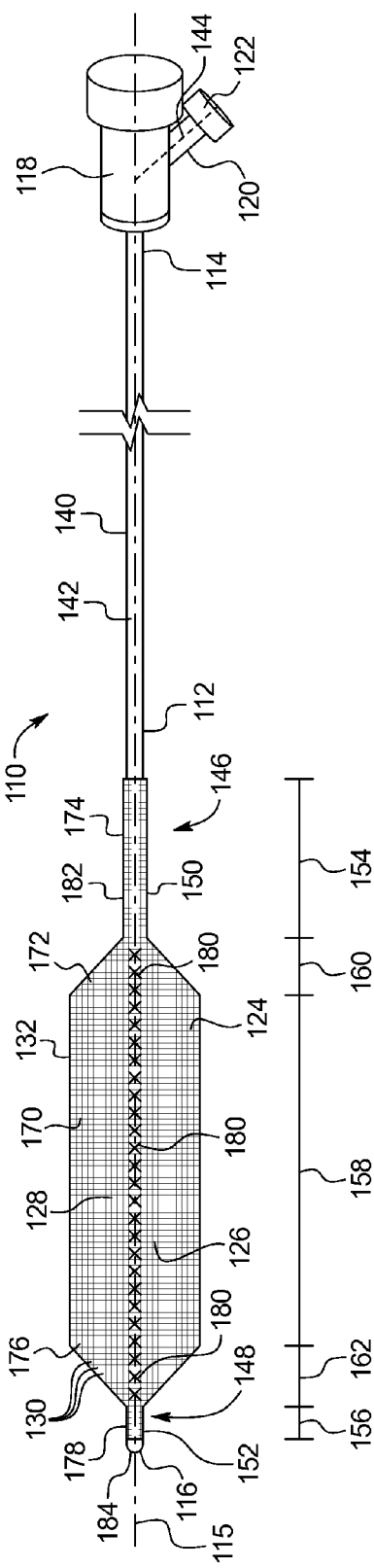
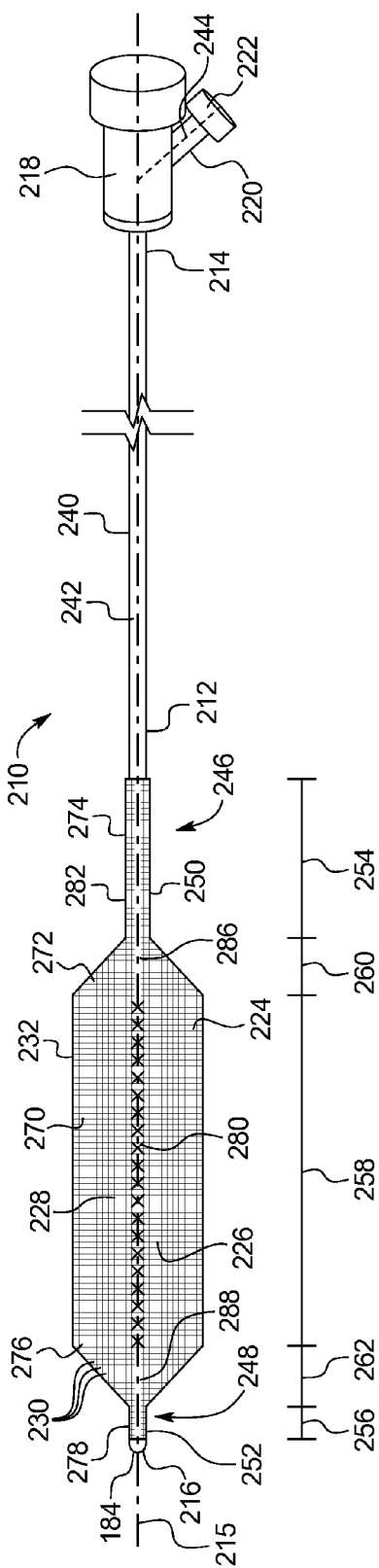

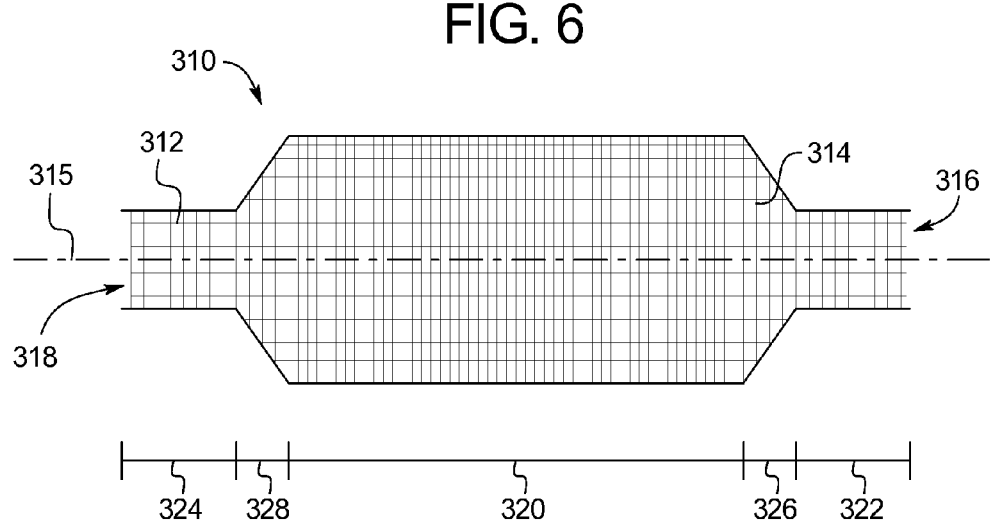
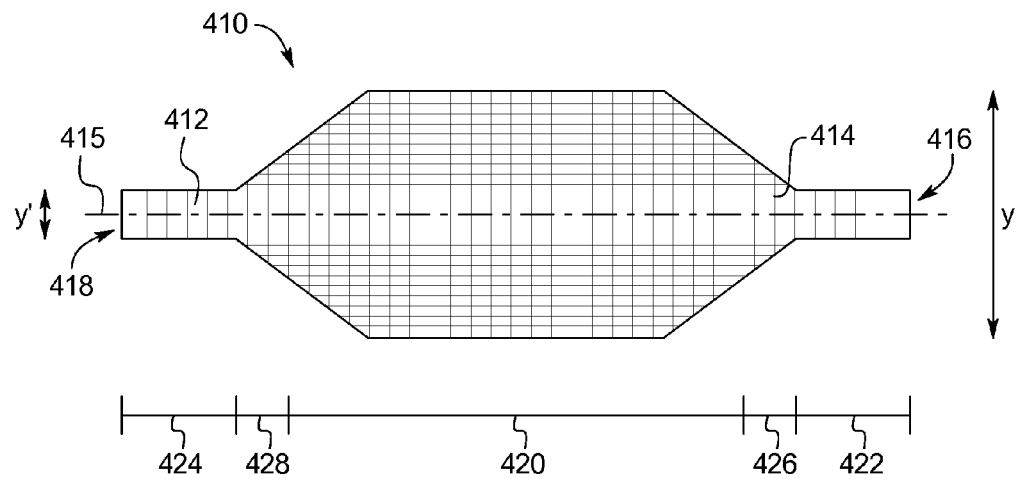

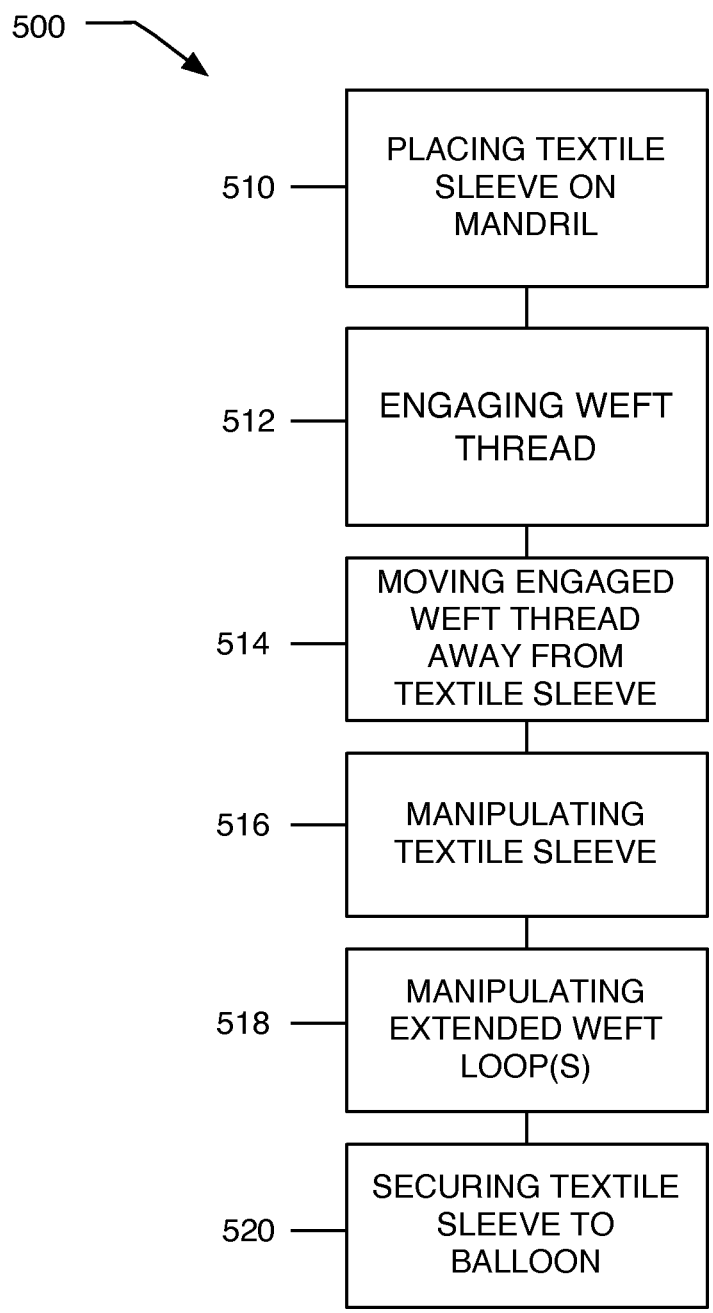

TEXTILE BALLOON CATHETERS

FIELD

The disclosure relates to medical devices. More particularly, the disclosure relates to balloon catheters useful in intraluminal treatment procedures on animals, such as human beings, components useful in the making of catheters, and methods of making catheters.

BACKGROUND

In the pursuit of catheters having expandable balloons with higher rated burst pressures and relatively thin wall thicknesses, artisans have developed catheters that include a textile component. While the development of textile-reinforced high-pressure balloon catheters has provided desirable balloon performance characteristics, the inclusion of textiles has introduced new challenges to the manufacturing of balloon catheters. As a result, a need remains for new textile balloon catheters and methods of making textile balloon catheters.

BRIEF SUMMARY OF SELECTED EXAMPLES

Catheters, catheter components, and methods of making catheters are described.

An example catheter comprises an elongate member having a proximal end, a distal end, a main body extending between the proximal end and the distal end, and a longitudinal axis, the main body defining a lumen; a balloon having uninflated and inflated configurations, the balloon secured to the elongate member and defining an interior chamber in communication with the lumen such that movement of fluid from the lumen into the interior chamber moves the balloon from the uninflated configuration to the inflated configuration and movement of fluid from the interior chamber of the balloon into the lumen moves the balloon from the inflated configuration to the uninflated configuration; the balloon having balloon proximal and balloon distal neck portions secured to the elongate member, a balloon body portion disposed between the balloon proximal and balloon distal neck portions and defining a maximum outer diameter of the balloon when the balloon is in the inflated configuration, a balloon proximal cone portion disposed between the balloon body portion and the balloon proximal neck portion, and a balloon distal cone portion disposed between the balloon body portion and the balloon distal neck portion; and a textile sleeve secured to the balloon, the textile sleeve having a textile sleeve body portion disposed on the balloon body portion, a textile sleeve proximal neck portion disposed on the balloon proximal neck portion, and a textile sleeve distal neck portion disposed on the balloon distal neck portion. The textile sleeve comprises a warp thread and at least one weft thread, the at least one weft thread defining a first set of circumferential loops in the textile sleeve body portion and a second set of circumferential loops in the textile sleeve proximal neck portion. A circumferential loop of the second set of circumferential loops extends only partially around the balloon proximal neck portion.

Another example catheter comprises an elongate member having a proximal end, a distal end, a main body extending between the proximal end and the distal end, and a longitudinal axis, the main body defining a lumen; a balloon having uninflated and inflated configurations, the balloon secured to the elongate member and defining an interior chamber in communication with the lumen such that movement of fluid from the lumen into the interior chamber moves the balloon from the uninflated configuration to the inflated configuration and movement of fluid from the interior chamber of the balloon into the lumen moves the balloon from the inflated configuration to the uninflated configuration; the balloon having balloon proximal and balloon distal neck portions secured to the elongate member, a balloon body portion disposed between the balloon proximal and balloon distal neck portions and defining a maximum outer diameter of the balloon when the balloon is in the inflated configuration, a balloon proximal cone portion disposed between the balloon body portion and the balloon proximal neck portion, and a balloon distal cone portion disposed between the balloon body portion and the balloon distal neck portion; and a textile sleeve secured the balloon, the textile sleeve having a textile sleeve body portion disposed on the balloon body portion, a textile sleeve proximal neck portion disposed on the balloon proximal neck portion, and a textile sleeve distal neck portion disposed on the balloon distal neck portion. The textile sleeve comprises a warp thread and at least one weft thread, the at least one weft thread defining a first set of circumferential loops in the textile sleeve body portion and a second set of circumferential loops in the textile sleeve proximal neck portion. A circumferential loop of the second set of circumferential loops includes two free ends of the at least one weft thread knotted together.

Another example catheter comprises an elongate member having a proximal end, a distal end, a main body extending between the proximal end and the distal end, and a longitudinal axis, the main body defining a lumen; a balloon having uninflated and inflated configurations, the balloon secured to the elongate member and defining an interior chamber in communication with the lumen such that movement of fluid from the lumen into the interior chamber moves the balloon from the uninflated configuration to the inflated configuration and movement of fluid from the interior chamber of the balloon into the lumen moves the balloon from the inflated configuration to the uninflated configuration; the balloon having balloon proximal and balloon distal neck portions secured to the elongate member, a balloon body portion disposed between the balloon proximal and balloon distal neck portions and defining a maximum outer diameter of the balloon when the balloon is in the inflated configuration, a balloon proximal cone portion disposed between the balloon body portion and the balloon proximal neck portion, and a balloon distal cone portion disposed between the balloon body portion and the balloon distal neck portion; and a textile sleeve secured the balloon, the textile sleeve having a textile sleeve body portion disposed on the balloon body portion, a textile sleeve proximal neck portion disposed on the balloon proximal neck portion, and a textile sleeve distal neck portion disposed on the balloon distal neck portion. The textile sleeve comprises a warp thread and at least one weft thread, the at least one weft thread defining a first set of circumferential loops in the textile sleeve body portion and a second set of circumferential loops in the textile sleeve proximal neck portion. A circumferential loop of the second set of circumferential loops forms an extended weft loop that is wrapped around the textile sleeve.

An example method of making a catheter comprises placing a textile sleeve having a plurality of warp threads and at least one weft thread on a mandril; engaging a weft thread of the textile sleeve with a tool; moving the engaged weft thread away from the remainder of the textile sleeve to form an extended weft loop; manipulating the extended weft loop; securing the textile sleeve to a balloon; and securing the balloon to an elongate member defining a lumen such that movement of fluid through the lumen moves the balloon between inflated an uninflated configurations.

Another example method of making a catheter comprises securing a textile sleeve having at least one extended weft loop to a balloon; and securing the balloon to an elongate member defining a lumen such that movement of fluid through the lumen moves the balloon between inflated an uninflated configurations.

Another example method of making a catheter comprises moving a weft thread away from the remainder of a textile sleeve comprising the weft thread to form an extended weft loop; securing the textile sleeve to a balloon; and securing the balloon to an elongate member defining a lumen such that movement of fluid through the lumen moves the balloon between inflated an uninflated configurations.

DESCRIPTION OF FIGURES

FIG. 1 is a perspective view, partially broken away, of a first example catheter.

FIG. 2 is a side view, partially broken away, of the distal end of the catheter illustrated in FIG. 1.

FIG. 3A is a magnified view of a portion of the first example catheter.

FIG. 3B is a magnified view of a portion of an alternative catheter.

FIG. 3C is a magnified view of a portion of another alternative catheter.

FIG. 4 is a perspective view, partially broken away, of a second example catheter.

FIG. 5 is a perspective view, partially broken away, of a third example catheter.

FIG. 6 is a top view of an example textile sleeve useful in the making of a catheter.

FIG. 7 is a top view of a second example textile sleeve useful in the making of a catheter.

FIG. 8 is a flowchart representation of an example method of making a catheter.

DESCRIPTION OF SELECTED EXAMPLES

Figure 9A:
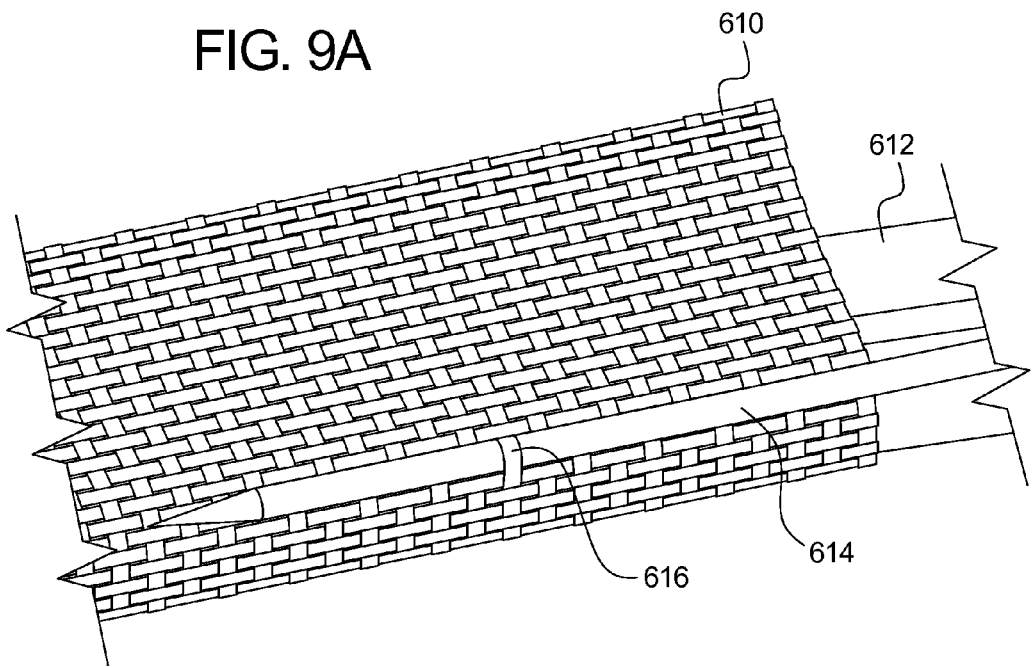
FIG. 9A is a schematic illustration of a textile sleeve with a weft thread engaged.

The following detailed description and the appended drawings describe and illustrate various example textile balloon catheters and methods of making textile balloon catheters useful in intraluminal treatment procedures on animals, such as human beings. The description and illustration of these examples are provided to enable one skilled in the art to make and use a catheter. They are not intended to limit the scope of the claims in any manner.

As used herein, the term "warp thread" refers to a thread in a textile element that extends generally along a longitudinal axis extending from a proximal end to a distal end of the textile element.

As used herein, the term "weft thread" refers to a thread in a textile element that extends circumferentially, partially circumferentially, helically, partially helically, or otherwise around or partially around a longitudinal axis extending from a proximal end to a distal end of the textile element and is woven with one or more warp threads.

As used herein, the term "thread" refers to a filament element having a length that is several times greater than its width. The term does not require any particular material or properties.

As used herein, the term "textile" refers to a woven element comprising warp threads and at least one weft thread.

As used herein, the term "picks per inch" refers to the linear density of weft thread loops in a referenced axial portion of a textile.

As used herein, the term "ends per inch" refers to the linear density of warp threads across a width of a textile that lies on a plane disposed orthogonal to the longitudinal axis of the textile.

As used herein, the term "sleeve" refers to an element that wholly or partially surrounds another element. The term does not require that the element be the radially outermost element in a structure and includes structural arrangements in which the element is radially outward of the surrounded element as well as arrangements in which the element is integrated with the surrounded element.

As used herein, the term "engaging" refers to an action of making contact between two referenced items that is sufficient to allow one of the items to move the other of the items when a force is applied to it. The term does not require any specific type or duration of contact between the items.

FIGS. 1, 2 and 3A illustrate an example catheter 10. The catheter 10 includes an elongate shaft 12 extending between a proximal end 14 and a distal end 16. A longitudinal axis 15 extends from the proximal end 14 to the distal end 16. A hub 18 is disposed on the proximal end 14 and includes sidearm 20 and connector 22. A balloon 24 is attached to a distal portion of the elongate shaft 12 adjacent the distal end 16. The balloon 24 defines an interior chamber 26 and has uninflated and inflated configurations. FIG. 1 illustrates the balloon 24 in the inflated configuration. A textile sleeve 28 is secured to the balloon 24 and surrounds the balloon 24. The textile sleeve 28 comprises a plurality of warp threads 30 extending along the longitudinal axis 15 and a weft thread 32 extending circumferentially around the longitudinal axis 15. The longitudinal axis 15 of the catheter 10 is also a longitudinal axis of the balloon 24 and a longitudinal axis of the textile sleeve 28.

The elongate shaft 12 comprises a main body 40 that extends along the entire length of the elongate shaft 12, from the proximal end 14 to the distal end 16. The main body 40 is a solid member that defines an inflation 42 lumen that extends along an axial length of the elongate shaft 12. The inflation lumen 42 is in communication with the interior chamber 26 of the balloon 24 and a port lumen 44 defined by the sidearm 20. Passage of fluid through the port 44 and inflation 42 lumens, such as fluid in a syringe or other device secured to the connector 22, inflates and deflates the balloon 24, moving it between its inflated and deflated configurations. As such, the inflation lumen 42 extends substantially along the entire length of the elongate shaft 12, from the proximal end 14 to a point on the longitudinal axis 15 of the elongate shaft 12 that lies within the interior chamber 26 of the balloon 24.

While the elongate shaft 12 of the illustrated embodiment includes only a single lumen, it is noted that a catheter according to an embodiment can include an elongate member that defines any suitable number of additional lumens having any desired function. For example, a catheter can include a main body that, in addition to an inflation lumen, defines a guidewire lumen that extends along a portion of the longitudinal axis of the catheter or along the entire longitudinal axis, from the proximal end to the distal end. As is known in the art, a guidewire lumen can be included if it is desirable to allow the catheter to be navigated over a guidewire that has been placed within a body vessel of an animal, such as a human being, within which the catheter is to be used. As noted above, a catheter according to a particular embodiment can include a lumen that extends along only a portion of the axial length of the elongate shaft. Thus, a guidewire lumen that extends along only a portion of the elongate shaft can be included in a catheter according to a particular embodiment, adapting that catheter for rapid exchange or short wire uses.

The inflation lumen 42, and indeed each lumen included in a catheter according to a particular embodiment, can have any suitable cross-sectional shape and configuration and a skilled artisan will be able to select a suitable shape and configuration for each lumen in a catheter according to a particular embodiment based on various considerations, including the intended use of each of the lumens. Also, the inflation lumen 42 and any other included lumen can have any suitable inner diameter or other measurement of cross-sectional size. Furthermore, the inflation lumen 42 and any other included lumens can be arranged within the main body of the elongate shaft in any suitable manner and a skilled artisan will be able to select a suitable arrangement for the lumens in a catheter according to a particular embodiment based on various considerations, including the relative sizes of the lumens and any desired flexibility of the elongate shaft.

While the illustrated catheter 10 includes an attached hub 18, it is noted that the inclusion of accessory components, such as the illustrated hub 18, is considered optional. Indeed, an embodiment of a catheter can include only an elongate member, a balloon and a textile sleeve. If inclusion of accessory components is desired, though, for a catheter according to a particular embodiment, any suitable catheter accessory component can be included, such as connectors, ports, valves, other types of hubs, and any other suitable catheter accessory component now known or later developed.

The balloon 24 is attached to elongate member 12 between the proximal end 14 and the distal end 16 of the elongate member 12 at proximal junction 46 and distal junction 48. The balloon 24 has a balloon proximal end 50 and a balloon distal end 52. The balloon 24 has a proximal neck 54 and a distal neck 56, each of which is closely fit to the outer circumference of the elongate member 12. As best illustrated in FIG. 2, the balloon 24 has a body 58 that has the maximum outer diameter of the balloon 24 when in the inflated configuration. A proximal cone 60 transitions from the proximal neck 54 to the body 58 and a distal cone 62 transitions from the distal neck 56 to the body 58. The interior surface of the balloon 24 and the portion of the exterior surface of elongate member 12 disposed within balloon 24 define balloon chamber 26 that is adapted to receive a fluid such that balloon 24 can be moved between a first deflated configuration and second inflated configuration. Balloon 24 is attached to elongate member 12 such that an opening defined by the elongate member 12 places the inflation lumen 42 in communication with balloon chamber 26. With this structural arrangement, balloon 24 is adapted to move between a first, deflated configuration and a second, inflated configuration as fluid is moved into and out of balloon chamber 26 via the inflation lumen 42. FIGS. 1 and 2 each illustrate the balloon 24 in the inflated configuration.

A user inflates balloon 24 by introducing a fluid, such as saline, into inflation lumen 42 until the fluid passes into balloon chamber 26. The resulting pressure placed on the inner surface of the balloon 24 by the fluid causes the balloon 24 to inflate and adopt the second, inflated configuration. To move the balloon 24 to the first, deflated configuration, vacuum pressure can be applied to inflation lumen 42 to remove fluid located within the balloon chamber 26, resulting in the balloon 24 collapsing and adopting the first, deflated configuration.

Balloon proximal junction 46 and balloon distal junction 48 can comprise any suitable attachment between elongate member 12 and balloon 24, and skilled artisans will be able to select a suitable attachment between a balloon and an elongate member for a catheter according to a particular embodiment based on various considerations, including the materials forming the elongate member and balloon. Example attachments considered suitable between an elongate member and a balloon include, but are not limited to, attachments formed by heat fusing, using adhesives, mechanical connections, and any other method considered suitable for a particular application.

The textile sleeve 28 is secured to and surrounds the balloon 24. The textile sleeve 28 comprises a plurality of warp threads 30 extending along, parallel to, or substantially parallel to the longitudinal axis 15 and a weft thread 32 extending circumferentially around the longitudinal axis 15. The illustrated embodiment includes a single weft thread 32 that is woven with a plurality of warp threads 30, but any suitable number of weft threads can be used in a textile sleeve for a catheter according to a particular embodiment.

The textile sleeve 28 can be secured to the balloon 24 in any suitable manner, and an attachment between the textile sleeve 28 and the balloon 24 can comprise any suitable attachment. A skilled artisan will be able to select a suitable attachment for a catheter according to a particular embodiment based on various considerations, including the material (s) of the textile sleeve and the balloon. Examples of suitable attachments include, but are not limited to, heat-induced fusion of a balloon and textile sleeve, an adhesive attachment, such as a chemical bond formed by applying an adhesive to a surface of a balloon and/or a surface of a textile sleeve prior to establishing contact between the two elements, or a mechanical bond, such as a bond formed by heating and subsequently cooling a textile sleeve and/or an outer surface of a balloon to allow the two elements to physically connect to each other. Alternatively, a chemical bond formed between an adhesive and thread or balloon material can be used as an attachment between a textile sleeve and a balloon in a particular embodiment. Also, a coating can be applied to a textile sleeve and balloon assembly to secure a textile sleeve to a balloon in a particular embodiment.

As best illustrated in FIG. 2, the textile sleeve 28 in the illustrated embodiment is disposed radially outward of the balloon 24. In this embodiment, the inner surface of the textile sleeve 28 is secured to the outer surface of the balloon 24. It is noted, though, that the textile sleeve in catheters according to particular embodiments can be integrated with the material that forms the balloon. For example, the textile sleeve and balloon can be heated such that the textile sleeve fuses with the material of the balloon. In these embodiments, some material of the balloon may actually be disposed radially outward of the textile sleeve. For example, some material of the balloon component of a catheter according to these embodiments may be disposed within one or more spaces formed by the weaving of one or more warp threads with one or more weft threads of the textile sleeve component. Indeed, some material of the balloon may extend through these spaces and, ultimately, over a portion of the textile sleeve component.

The weft thread 32 defines a series of circumferential loops that extend around the longitudinal axis 15 of the elongate member 12 and indeed around the balloon 12 and/or the elongate member 12. The circumferential loops 70 in the portion of the textile sleeve 28 that is secured to the body 58 of the balloon 24 are larger in diameter than the circumferential loops 72 in the portion of the textile sleeve 28 that is secured to the proximal cone 60. In turn, the circumferential loops 70, 72 in these portions of the textile sleeve 28 are larger in diameter than the circumferential loops 74 in the portion of the textile sleeve 28 that is secured to the proximal neck 54. The circumferential loops 70 in the portion of the textile sleeve 28 that is secured to the body 58 of the balloon 24 are larger in diameter than the circumferential loops 76 in the portion of the textile sleeve 28 that is secured to the distal cone 62. In turn, the circumferential loops 70, 76 in these portions of the textile sleeve 28 are larger in diameter than the circumferential loops 78 in the portion of the textile sleeve 28 that is secured to the distal neck 56.

The circumferential loops 70, 72, 74, 76, 78 of the various relative sizes can be formed in any suitable manner using any suitable technique. In the example embodiment, as best illustrated in FIG. 3A, the weft thread 32 in the portion of the textile sleeve 28 secured to the proximal neck 54 includes a series of knots 80. As described in more detail below, each knot 80 can be formed after cutting an extended weft loop and forming the knot 80 with the ends created by the cutting. Also as described in more detail below, the extended weft loop can be formed by pulling a section of the weft thread 32 until it is drawn tight against the elongate member 12.

FIG. 3B illustrates an alternative embodiment. The catheter 10' of this alternative embodiment is identical to the catheter 10 described above, except for having circumferential loops 74' that have a different structure than the circumferential loops 74 of catheter 10. In this embodiment, each of the circumferential loops 74' in the portion of the textile sleeve 28' secured to the proximal neck 54 is a partial circumferential loop and includes two free ends. The free ends of the series of circumferential loops 74' forms a gap 82' in the portion of the textile sleeve 28' secured to the proximal neck 54. As described in more detail below, the series of partial circumferential loops 74' and the gap 82' can be formed after cutting a series of extended weft loops formed in the weft thread 32' tightly against the elongate member 12 and leaving the resulting ends free. In the illustrated embodiment, each of the circumferential loops 74' in the portion of the textile sleeve 28' secured to the proximal neck 54 is a partial circumferential loop and includes two free ends. It is noted, though, that a catheter according to a particular embodiment can have any desired number of circumferential loops having free ends in a portion of a textile sleeve that is secured to a particular portion of a balloon, such as a neck, body or cone portion, and a skilled artisan will be able to select an appropriate number of circumferential loops having free ends based on various considerations, such as the length of the portion of the balloon to which the portion of the textile sleeve is or is to be secured, the material forming the textile sleeve, and other considerations. Examples of suitable numbers of circumferential loops having free ends in a portion of a textile sleeve that is secured to a particular portion of a balloon include all circumferential loops in the portion of the textile sleeve, less than all circumferential loops in the portion of the textile sleeve, one of the circumferential loops in the portion of the textile sleeve, two circumferential loops in the portion of the textile sleeve, a plurality of circumferential loops in the portion of the textile sleeve, three circumferential loops in the portion of the textile sleeve, and more than three circumferential loops in the portion of the textile sleeve. A suitable number of circumferential loops having free ends can be represented as a percentage of all circumferential loops in the portion of the textile sleeve. For example, between about 1 and 100% of the circumferential loops in the portion of the textile sleeve can have free ends. Also, between about 1 and 75% of the circumferential loops in the portion of the textile sleeve can have free ends. Also, between about 1 and 50% of the circumferential loops in the portion of the textile sleeve can have free ends. Also, between about 1 and 25% of the circumferential loops in the portion of the textile sleeve can have free ends. Also, between about 1 and 10% of the circumferential loops in the portion of the textile sleeve can have free ends. Also, between about 1 and 5% of the circumferential loops in the portion of the textile sleeve can have free ends. Also, between about 5 and 20% of the circumferential loops in the portion of the textile sleeve can have free ends. Also, between about 10 and 15% of the circumferential loops in the portion of the textile sleeve can have free ends.

In an embodiment that includes one or more circumferential loops having free ends, the resulting gap in the associated portion of the textile sleeve can have any suitable orientation relative to the elongate member of the embodiment. For example, in the embodiments illustrated in FIG. 3B, the gap 82' extends axially along the elongate member 12. Alternatively, the gap in an embodiment can extend at a non-linear angle to the elongate member of the embodiment, effectively orienting the gap to extend around the elongate member of the embodiment along a helical path. In these embodiments, the gap can extend along a helical path for a complete helical turn around the elongate member of the embodiment, along a portion of a helical turn around the elongate member of the embodiment, or along two, three, a plurality, or more helical turns around the elongate member of the embodiment.

FIG. 3C illustrates another alternative embodiment. The catheter 10" of this alternative embodiment is identical to the catheter 10 described above, except for having circumferential loops 74" that have a different structure that the circumferential loops 74 of catheter 10. In this embodiment, each of the circumferential loops 74" in the portion of the textile sleeve 28" secured to the proximal neck 54 extends around the proximal neck 54 and the elongate member 12 more than a single revolution. In the illustrated embodiment, each of the circumferential loops 74" is helically wound around the proximal neck 54 and the elongate member 12 multiple times. As described in more detail below, each of the helically-wound circumferential loops 74" can be formed by pulling a section of the weft thread 32" until it is drawn tight against the elongate member 12 and wrapping the resulting extended weft loop around the proximal neck 54 and elongate member 12. In the illustrated embodiment, each of the circumferential loops 74" in the portion of the textile sleeve 28" secured to the proximal neck 54 extends around the proximal neck 54 and the elongate member 12 more than a single revolution. It is noted, though, that a catheter according to a particular embodiment can have any desired number of circumferential loops that extend multiple times around a portion of a textile sleeve that is secured to a particular portion of a balloon, such as a neck, body or cone portion, and a skilled artisan will be able to select an appropriate number of circumferential loops that extend multiple times around the textile sleeve based on various considerations, such as the length of the portion of the balloon to which the portion of the textile sleeve is or is to be secured, the material forming the textile sleeve, and other considerations. Examples of suitable numbers of circumferential loops that extend multiple times around a portion of a textile sleeve that is secured to a particular portion of a balloon include all circumferential loops in the portion of the textile sleeve, less than all circumferential loops in the portion of the textile sleeve, one of the circumferential loops in the portion of the textile sleeve, two circumferential loops in the portion of the textile sleeve, a plurality of circumferential loops in the portion of the textile sleeve, three circumferential loops in the portion of the textile sleeve, and more than three circumferential loops in the portion of the textile sleeve. A suitable number of circumferential loops that extend multiple times around the textile sleeve can be represented as a percentage of all circumferential loops in the portion of the textile sleeve. For example, between about 1 and 100% of the circumferential loops in the portion of the textile sleeve can extend multiple times around the textile sleeve. Also, between about 1 and 75% of the circumferential loops in the portion of the textile sleeve can extend multiple times around the textile sleeve. Also, between about 1 and 50% of the circumferential loops in the portion of the textile sleeve can extend multiple times around the textile sleeve. Also, between about 1 and 25% of the circumferential loops in the portion of the textile sleeve can extend multiple times around the textile sleeve. Also, between about 1 and 10% of the circumferential loops in the portion of the textile sleeve can extend multiple times around the textile sleeve Also, between about 1 and 5% of the circumferential loops in the portion of the textile sleeve can extend multiple times around the textile sleeve. Also, between about 5 and 20% of the circumferential loops in the portion of the textile sleeve can extend multiple times around the textile sleeve. Also, between about 10 and 15% of the circumferential loops in the portion of the textile sleeve can extend multiple times around the textile sleeve.

In an embodiment that includes one or more circumferential loops that extend around a portion of the textile sleeve and the elongate member more than a single revolution, any suitable number of revolutions around the portion of the textile sleeve and the elongate member can be used, including two, a plurality, three, and more revolutions. The structure illustrated in FIG. 3C illustrates an example number of revolutions.

In an embodiment that includes one or more circumferential loops that extend around a portion of the textile sleeve and the elongate member more than a single revolution, the circumferential loops can be oriented around the textile sleeve and elongate member at any suitable angle relative to the elongate member, including orthogonal and non-orthogonal angles relative to the lengthwise axis of the elongate member. An angle relative to the lengthwise axis of the elongate member that orients the circumferential loop along a helical path around the elongate member, as illustrated in FIG. 3C, can be used.

While the illustrated embodiments show various structures associated with circumferential loops in the portion of the textile sleeve that is secured to the proximal neck of the balloon, it is noted that a catheter according to a particular embodiment can include any suitable combination of the illustrated structures and/or other suitable structures in other portions of the textile sleeve, including the portions of the textile sleeve that are secured to the proximal cone, body, distal cone, and/or distal neck portions of the balloon components of the catheter. Inclusion of an inventive structure in the proximal neck portion of the textile sleeve in a catheter according to a particular embodiment is considered advantageous at least because that portion provides sufficient surface area to achieve a desired degree of reinforcement. Including an inventive structure in other portions can enhance the effect and/or can be used to achieve a desired localization of structural properties, an example of which is described below.

For example, FIG. 4 illustrates a second example catheter 110. The catheter 110 is similar to the first example catheter 10 described above, except as indicated below. Thus, the catheter 110 includes an elongate shaft 112 extending between a proximal end 114 and a distal end 116. A longitudinal axis 115 extends from the proximal end 114 to the distal end 116. A hub 118 is disposed on the proximal end 114 and includes sidearm 120 and connector 122. A balloon 124 is attached to a distal portion of the elongate shaft 112 adjacent the distal end 116. The balloon 124 defines an interior chamber 126 and has uninflated and inflated configurations. FIG. 4 illustrates the balloon 124 in the inflated configuration. A textile sleeve 128 is secured to the balloon 124 and surrounds the balloon 124. The textile sleeve 128 comprises a plurality of warp threads 130 extending along the longitudinal axis 115 and at least one weft thread 132 extending circumferentially around the longitudinal axis 115. The longitudinal axis 115 of the catheter 110 is also a longitudinal axis of the balloon 124 and a longitudinal axis of the textile sleeve 128. The elongate shaft 112 comprises a main body 140 that extends along the entire length of the elongate shaft 112, from the proximal end 114 to the distal end 116. The main body 140 is a solid member that defines an inflation lumen 142 that extends along an axial length of the elongate shaft 112. The inflation lumen 142 is in communication with the interior chamber 126 of the balloon 124 and a port lumen 144 defined by the sidearm 120. The balloon 124 is attached to elongate member 112 at proximal junction 146 and distal junction 148. The balloon 124 has a balloon proximal end 150 and a balloon distal end 152. The balloon 124 has a proximal neck 154 and a distal neck 156, each of which is closely fit to the outer circumference of the elongate member 112. Also, the balloon 124 has a body 158 that has the maximum outer diameter of the balloon 124 when in the inflated configuration. A proximal cone 160 transitions from the proximal neck 154 to the body 158 and a distal cone 162 transitions from the distal neck 156 to the body 158. The weft thread 132 of the textile sleeve 128 defines a series of circumferential loops that extend around the longitudinal axis 115 of the elongate member 112 and indeed around the balloon 112 and/or the elongate member 112.

In this embodiment, the portion of the textile sleeve 128 that is secured to the proximal neck 154 portion of the balloon 124 includes a series of circumferential loops 174, each of which is a partial circumferential loop that includes two free ends. The free ends of the series of circumferential loops 174 forms a gap 182 in the portion of the textile sleeve 128 secured to the proximal neck 154 of the balloon 124. Similarly, the portion of the textile sleeve 128 that is secured to the distal neck 156 portion of the balloon 124 includes a series of circumferential loops 178, each of which is a partial circumferential loop that includes two free ends. The free ends of the series of circumferential loops 178 forms a gap 184 in the portion of the textile sleeve 128 secured to the distal neck 156 of the balloon 124.

In contrast, the circumferential loops 170, 172, 176 of the portions of the textile sleeve 128 that are secured to the body 158, proximal cone 160 and distal cone 162 portions of the balloon 124, respectively, includes a series of knots 180. As described in more detail below, each knot 180 can be formed after cutting an extended weft loop and forming the knot 180 with the ends created by the cutting. The inventors believe that the inclusion of knots in the portions of the textile sleeve 128 that are secured to the body 158, proximal cone 160 and distal cone 162 portions of the balloon 124, while leaving gaps 182, 184 in the portions of the textile sleeve 128 secured to the proximal neck 154 and distal neck 156 portions of the balloon 124, respectively, may be advantageous. Inclusion on knots in this manner provides more strength for reinforcement in the area where the balloon experiences the most stress during use. Such strength is not necessary in the proximal and distal neck portions, where removal of excess textile material can be desirable for attachment of the balloon to underlying materials.

FIG. 5 illustrates a third example catheter 210. The catheter 210 is similar to the first example catheter 10 described above, except as indicated below. Thus, the catheter 210 includes an elongate shaft 212 extending between a proximal end 214 and a distal end 216. A longitudinal axis 215 extends from the proximal end 214 to the distal end 216. A hub 218 is disposed on the proximal end 214 and includes sidearm 220 and connector 222. A balloon 224 is attached to a distal portion of the elongate shaft 212 adjacent the distal end 216. The balloon 224 defines an interior chamber 226 and has uninflated and inflated configurations. FIG. 5 illustrates the balloon 224 in the inflated configuration. A textile sleeve 228 is secured to the balloon 224 and surrounds the balloon 224. The textile sleeve 228 comprises a plurality of warp threads 230 extending along the longitudinal axis 215 and at least one weft thread 232 extending circumferentially around the longitudinal axis 215. The longitudinal axis 215 of the catheter 210 is also a longitudinal axis of the balloon 224 and a longitudinal axis of the textile sleeve 228. The elongate shaft 212 comprises a main body 240 that extends along the entire length of the elongate shaft 212, from the proximal end 214 to the distal end 216. The main body 240 is a solid member that defines an inflation lumen 242 that extends along an axial length of the elongate shaft 212. The inflation lumen 242 is in communication with the interior chamber 226 of the balloon 224 and a port lumen 244 defined by the sidearm 220. The balloon 224 is attached to elongate member 212 at proximal junction 246 and distal junction 248. The balloon 224 has a balloon proximal end 250 and a balloon distal end 252. The balloon 224 has a proximal neck 254 and a distal neck 256, each of which is closely fit to the outer circumference of the elongate member 212. Also, the balloon 224 has a body 258 that has the maximum outer diameter of the balloon 224 when in the inflated configuration. A proximal cone 260 transitions from the proximal neck 254 to the body 258 and a distal cone 262 transitions from the distal neck 256 to the body 258. The weft thread 232 of the textile sleeve 228 defines a series of circumferential loops that extend around the longitudinal axis 215 of the elongate member 212 and indeed around the balloon 212 and/or the elongate member 212.

In this embodiment, the portion of the textile sleeve 228 that is secured to the proximal neck 254 portion of the balloon 224 includes a series of circumferential loops 274, each of which is a partial circumferential loop that includes two free ends. The free ends of the series of circumferential loops 274 forms a gap 282 in the portion of the textile sleeve 228 secured to the proximal neck 254 of the balloon 224. Similarly, the portion of the textile sleeve 228 that is secured to the distal neck 256 portion of the balloon 224 includes a series of circumferential loops 278, each of which is a partial circumferential loop that includes two free ends. The free ends of the series of circumferential loops 278 forms a gap 284 in the portion of the textile sleeve 228 secured to the distal neck 256 of the balloon 224. Also in this embodiment, and in contrast to the embodiment illustrated in FIG. 4 and described above, the circumferential loops 272 of the portion of the textile sleeve 228 that is secured to the proximal cone 260 portion of the balloon 224 include a series of circumferential loops, each of which is a partial circumferential loop that includes two free ends. The free ends of the series of circumferential loops 272 forms a gap 286 in the portion of the textile sleeve 228 secured to the proximal cone 260 of the balloon 224. Similarly, the circumferential loops 276 of the portion of the textile sleeve 228 that is secured to the distal cone 262 portion of the balloon 224 include a series of circumferential loops, each of which is a partial circumferential loop that includes two free ends. The free ends of the series of circumferential loops 276 forms a gap 288 in the portion of the textile sleeve 228 secured to the distal cone 262 of the balloon 224.

In contrast, the circumferential loops 270 of the portion of the textile sleeve 228 that is secured to the body 258 portion of the balloon 224 includes a series of knots 280. As described in more detail below, each knot 280 can be formed after cutting an extended weft loop and forming the knot 280 with the ends created by the cutting. The inventors believe that the inclusion of knots in the portion of the textile sleeve 228 that is secured to the body 258 portion of the balloon 224, while leaving gaps 282, 284, 286, 288 in the portions of the textile sleeve 228 secured to the proximal neck 254, distal neck 256, proximal cone 260 and distal cone 262 portions of the balloon 224, respectively, may be suitable for use with balloons having localized compliance properties. For example, this structural arrangement may be suitable for use in a catheter having a balloon with a body portion that is non-compliant or that has relatively low compliance compared to other portions of the balloon, and that has one or more compliant cone portions.

All components of a catheter according to an embodiment can be made from any suitable material. Skilled artisans will be able to select appropriate materials for the components of a catheter according to a particular embodiment based on various considerations, including the nature of the body vessel within which the particular catheter is intended to be used. Examples of suitable materials include, but are not limited to, plastics and other materials currently used in the manufacture of conventional catheters, and newly-developed materials determined to be suitable for use in components of medical catheters.

The balloon component of a catheter according to an embodiment can be formed of any suitable material, and skilled artisans will be able to select a suitable material for a balloon in a catheter according to a particular embodiment based on various considerations, including the material(s) that form the elongate member in the catheter. Example materials considered suitable to form a balloon include, but are not limited to, biocompatible materials, materials that can be made biocompatible, flexible materials, substantially flexible materials, polymers, Pebax (Pebax is a registered trademark of Ato Chimie Corporation of Allee des Vosges, Courbevoie, France), nylon, polyethylene, polyurethane, other materials currently considered suitable for use as a balloon component in a medical catheter, and newly-developed materials determined to be suitable for use as a balloon component in a medical catheter. Furthermore, balloon 24 can comprise any suitable type of balloon, such as a compliant balloon, a non-compliant balloon, any other type of balloon currently considered suitable for use in a medical catheter, and any newly-developed type of balloon determined to be suitable for use in a medical catheter.

The textile sleeve component of a catheter according to an embodiment can be formed of any suitable material, and skilled artisans will be able to select a suitable material for a textile sleeve in a catheter according to a particular embodiment based on various considerations, including the material(s) that form the balloon in the catheter. Example materials considered suitable to form a textile sleeve include, but are not limited to, biocompatible materials, materials that can be made biocompatible, natural materials and synthetic materials. Examples of suitable materials include polyester threads, polyethylene threads, nylon threads, metallic wires, silk threads, and plastic threads. Threads formed of ultra high molecular weight polyethylene are also considered suitable. Threads formed of polytetrafluoroethylene (PTFE), threads formed of polyetheretherketone (PEEK), and threads formed of polyetherketoneketone (PEKK) are also considered suitable. Also, threads having a monofilament structure and threads having a multifilament structure are considered suitable. Furthermore, a textile sleeve can include threads that comprise the same or different materials and the same or different structures. For example, a textile sleeve can have warp and weft threads that comprise the same material or that comprise different materials and that have the same structure or that have different structures.

The textile sleeve component of a catheter according to an embodiment can have any suitable structure prior to being secured to a balloon during the making of the catheter, and skilled artisans will be able to select a suitable structure for a textile sleeve for inclusion in a catheter according to a particular embodiment based on various considerations, including any desired final structure of the textile sleeve relative to the balloon component of the catheter. The inventors have determined that a textile sleeve that has a localized density of circumferential loops defined by one or more weft threads that is lower in the area or areas along the longitudinal axis of the textile sleeve in which it is desired to reduce the cross-sectional diameter of the textile sleeve during the making of the catheter, as compared to a localized density of circumferential loops in another area or other areas along the longitudinal axis of the textile sleeve, is suitable for making catheters, such as the example catheters described and illustrated herein.

FIG. 6 illustrates an example textile sleeve 310 useful in the making of a catheter. The textile sleeve 310 is a circumferential body forming an interior cavity 311 that can receive a balloon or balloon precursor during the making of a catheter. The textile sleeve 310 includes a plurality of warp threads 312 extending along, parallel to, or substantially parallel to the longitudinal axis 315 and at least one weft thread 314 extending circumferentially around the longitudinal axis 315. The textile sleeve 310 defines a proximal opening 316 and an opposite distal opening 318, each of which provides access into the interior cavity 311. The textile sleeve 310 has a body portion 320 that extends along a portion of the longitudinal axis 315 and that has the largest outer diameter of the textile sleeve 310. Also, the textile sleeve 310 includes proximal 322 and distal 324 neck portions, which define the proximal 316 and distal 318 openings, respectively, and proximal 326 and distal 328 cone portions, each of which transitions from the relatively large outer diameter of the body portion 320 to the relatively small outer diameter of the respective proximal 322 and distal 324 neck portions.

The textile sleeve 310 includes localized weft densities, represented as picks per inch, that make the textile sleeve 310 suitable for use in the methods of making catheters described herein. For example, the textile sleeve 310 has a weft density extending along the body portion 320 that is greater than the weft density that extends along each of the proximal neck 322, distal neck 324, proximal cone 326 and distal cone 328 portions of the textile sleeve 310. While the illustrated textile sleeve 310 has a weft density extending along the body portion 320 that is greater than the weft density that extends along each of the proximal neck 322, distal neck 324, proximal cone 326 and distal cone 328 portions of the textile sleeve 310, it is noted that a textile sleeve according to an embodiment can have a weft density extending along the body portion of the textile sleeve that is greater than one or more of the proximal neck, distal neck, proximal cone, and distal cone portions of the textile sleeve.

Indeed, a textile sleeve according to an embodiment can have any suitable relative weft densities between the body and one or more of the proximal neck, distal neck, proximal cone and distal cone portions of the textile sleeve, and a skilled artisan will be able to select suitable relative and actual weft densities for the various portions of a textile sleeve according to a particular embodiment based on various considerations, including the overall size of the textile sleeve, the composition of the warp and weft threads, and any requirements or considerations of a method of making a catheter in which the textile sleeve is intended to be used. The inventors believe that a ratio of weft densities for a body portion of a textile sleeve to one or more other portions of a textile sleeve that is a proximal neck, distal neck, proximal cone or distal cone of the textile sleeve that is between about 10 to 1 and about 2 to 1 is suitable for use in the methods of making a catheter described below. Also, the inventors believe that a ratio of weft densities for a body portion of a textile sleeve to one or more other portion(s) of a textile sleeve that is a proximal neck, distal neck, proximal cone or distal cone of the textile sleeve that is between about 8 to 1 and about 2 to 1 is suitable for use in the methods of making a catheter described below. Also, the inventors believe that a ratio of weft densities for a body portion of a textile sleeve to one or more other portions of a textile sleeve that is a proximal neck, distal neck, proximal cone or distal cone of the textile sleeve that is between about 6 to 1 and about 2 to 1 is suitable for use in the methods of making a catheter described below. Also, the inventors believe that a ratio of weft densities for a body portion of a textile sleeve to one or more other portions of a textile sleeve that is a proximal neck, distal neck, proximal cone or distal cone of the textile sleeve that is between about 8 to 1 and about 5 to 1 is suitable for use in the methods of making a catheter described below. Also, the inventors believe that a ratio of weft densities for a body portion of a textile sleeve to one or more other portions of a textile sleeve that is a proximal neck, distal neck, proximal cone or distal cone of the textile sleeve that is between about 4 to 1 and about 2 to 1 is suitable for use in the methods of making a catheter described below. Also, the inventors believe that a ratio of weft densities for a body portion of a textile sleeve to one or more other portions of a textile sleeve that is a proximal neck, distal neck, proximal cone or distal cone of the textile sleeve that is between about 3 to 1 and about 2 to 1 is suitable for use in the methods of making a catheter described below. Also, the inventors believe that a ratio of weft densities for a body portion of a textile sleeve to one or more other portions of a textile sleeve that is a proximal neck, distal neck, proximal cone or distal cone of the textile sleeve that is about 5 to 1 is suitable for use in the methods of making a catheter described below. Also, the inventors believe that a ratio of weft densities for a body portion of a textile sleeve to one or more other portions of a textile sleeve that is a proximal neck, distal neck, proximal cone or distal cone of the textile sleeve that is about 4 to 1 is suitable for use in the methods of making a catheter described below. Also, the inventors believe that a ratio of weft densities for a body portion of a textile sleeve to one or more other portions of a textile sleeve that is a proximal neck, distal neck, proximal cone or distal cone of the textile sleeve that is about 3 to 1 is suitable for use in the methods of making a catheter described below. Also, the inventors believe that a ratio of weft densities for a body portion of a textile sleeve to one or more other portions of a textile sleeve that is a proximal neck, distal neck, proximal cone or distal cone of the textile sleeve that is about 2 to 1 is suitable for use in the methods of making a catheter described below. In one example, the inventors have determined that a textile sleeve having a body portion with a weft density of about 130 picks per inch and proximal and distal neck portions with a weft density of about 40 picks per inch is suitable for use in the methods of making a catheter described herein.

In addition, or in lieu of localized weft densities, a textile sleeve can have a warp density, represented as ends per inch, that varies at any point along the width of the textile sleeve, measured orthogonally or substantially orthogonally to the longitudinal axis of the textile sleeve. For example, FIG. 7 illustrates an example textile sleeve 410 useful in the making of a catheter. The textile sleeve 410 is a circumferential body forming an interior cavity 411 that can receive a balloon or balloon precursor during the making of a catheter. The textile sleeve 410 includes a plurality of warp threads 412 extending along, parallel to, or substantially parallel to the longitudinal axis 415 and at least one weft thread 414 extending circumferentially around the longitudinal axis 415. The textile sleeve 410 defines a proximal opening 416 and an opposite distal opening 418, each of which provides access into the interior cavity 411. The textile sleeve 410 has a body portion 420 that extends along a portion of the longitudinal axis 415 and that has the largest outer diameter of the textile sleeve 410. Also, the textile sleeve 410 includes proximal 422 and distal 424 neck portions, which define the proximal 416 and distal 418 openings, respectively, and proximal 426 and distal 428 cone portions, each of which transitions from the relatively large outer diameter of the body portion 420 to the relatively small outer diameter of the respective proximal 422 and distal 424 neck portions.

The textile sleeve 410 includes a localized warp density that makes the textile sleeve 410 suitable for use in the methods of making catheters described herein. The textile sleeve 410 has a lower warp density across the width y' of the proximal neck portion 422 and the distal neck portion 424, referred to as the neck portions warp density, than the warp density across the width y of the body portion, referred to as the body warp density, and the varying widths of the proximal cone portion 426 and the distal cone portion 428, referred to as the cone warp density. In the illustrated embodiment, the warp density across the width y' of the proximal neck 422 and distal neck 424 portions extends through the central portion of the proximal cone 426, distal cone 428, and body 420 portions, while the peripheral portions of the proximal cone 426, distal cone 428, and body 420 portions have higher warp densities, giving these portions higher overall warp densities than those of the proximal neck 422 and distal neck 424 portions. While any suitable relative warp densities can be used, it is noted that a warp density ratio of between about 2:1 and about 1:1 of the body warp density to the neck portions warp density is considered suitable. As an example, the inventors have determined that a warp density of about or exactly 83 ends per inch in the body portion and a warp density of about or exactly 63 ends per inch in the neck portions provides a suitable structure.

A catheter according to an embodiment can be made in any suitable manner and using any suitable technique. Skilled artisans will be able to select an appropriate technique for making a catheter according to a particular embodiment based on various considerations, including the nature of the materials used for the various components.

It is noted that a catheter produced by any of the inventive methods, including those described below, is considered to be an example embodiment of the invention.

FIG. 8 is a flowchart representation of an example method 500 of making a catheter. The steps of the method 500 can be performed in any suitable order and no order is implied by the order described below and/or illustrated in the figure, except where an explicit reference is made to another step.

An initial step 510 of the method 500 comprises placing a textile sleeve on a mandril. The textile sleeve can comprise any suitable textile sleeve, including those described herein. Also, the mandril can comprise any suitable mandril, including a metal rod, a plastic rod, and an elongate member that is a component of a catheter or a precursor of a component of a catheter.

Another step 512 comprises engaging a weft thread of the textile sleeve with a tool. Any suitable tool can be used to perform this step, including a finger or fingers, a needle and any other suitable tool. Furthermore, any suitable technique for engaging a weft thread with a tool can be used, and the technique need only result in making contact between the tool and the weft thread that enables the moving step 514 described below. For example, if the tool comprises a needle, this step 512 can be accomplished by placing the needle between a selected weft thread and other weft and warp threads such that the moving step 514 can be performed. It is believed to be advantageous to perform this step 512 by engaging only a single weft thread.

FIG. 9A illustrates an example textile sleeve 610 disposed on a mandril 612. A needle 614 is engaged with a single weft thread 616 after performance of step 512.

Figure 9B:
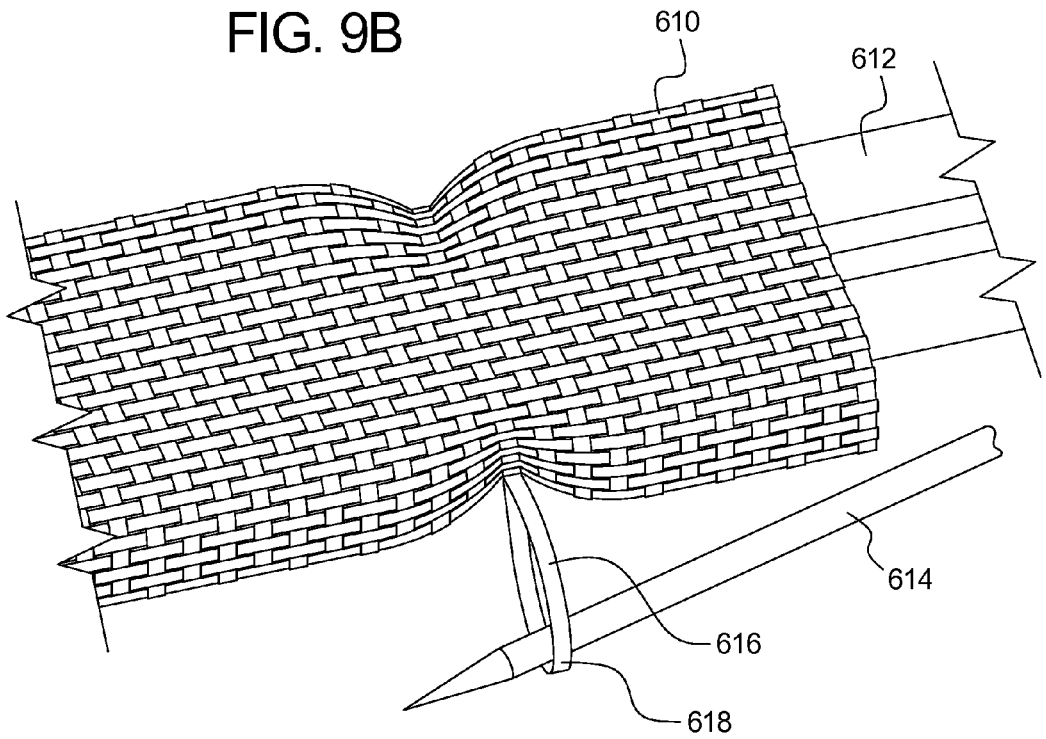
FIG. 9B is a schematic illustration of a textile sleeve with a selected weft thread being moved away from the remainder of the textile sleeve.

Another step 514 comprises moving the engaged weft thread away from the remainder of the textile sleeve to form an extended weft loop. This step can be performed in any suitable manner. For example, a force can be applied to the tool used in the engaging step 512 to cause it to move away from the textile sleeve and mandril such that an extended weft loop is formed. FIG. 9B shows an extended weft loop 618 after performance of this step 514. This step 514 can be performed to any suitable degree, typically measured by the size of the extended weft loop or the ability to continue moving the engaged weft thread away from the textile sleeve and the mandril. The inventors have determined that it is suitable to continue the moving of this step 514 until the engaged weft thread prevents further moving, typically due to being reduced to the smallest possible circumferential loop or circumferential loops around the mandril. Also, if it is desirable in a particular method to have loose ends formed in the extended weft loop, such as in the example catheters described above, the inventors have determined that it is suitable to continue this moving step 514, if possible, until the engaged weft thread breaks and the loose ends are formed.

FIG. 9B illustrates the example textile sleeve 610 after the engaged weft thread 616 has been moved away from the remainder of the textile sleeve 610. An extended weft loop 618 has formed as a result of the movement.

In some example methods, the step 512 of engaging a weft thread and the step 514 of moving the engaged weft thread away from the textile sleeve can be repeated a desired number of times, engaging a different weft thread or a different portion of a weft thread with each performance of the steps 512, 514 to produce a desired number of extended weft loops.

The step 514 of moving the engaged weft thread away from the remainder of the textile sleeve can produce a longitudinal gap in the textile sleeve as the extended weft loop or extended weft loops are formed. If the presence of a longitudinal gap is undesirable in the catheter being made, an optional step 516 or manipulating the textile sleeve to remove the longitudinal gap can be performed. If included, this step 516 can be performed using any suitable technique. A skilled artisan will be able to select a suitable technique for a particular method based on various considerations, including the nature of the material or materials of the textile sleeve. The inventors have determined that a simple digital manipulation of the warp and/or weft threads of the textile sleeve near and/or around the longitudinal gap is typically sufficient to remove a longitudinal gap or reduce a longitudinal gap to an acceptable size, configuration, and/or orientation.

Figure 9C:
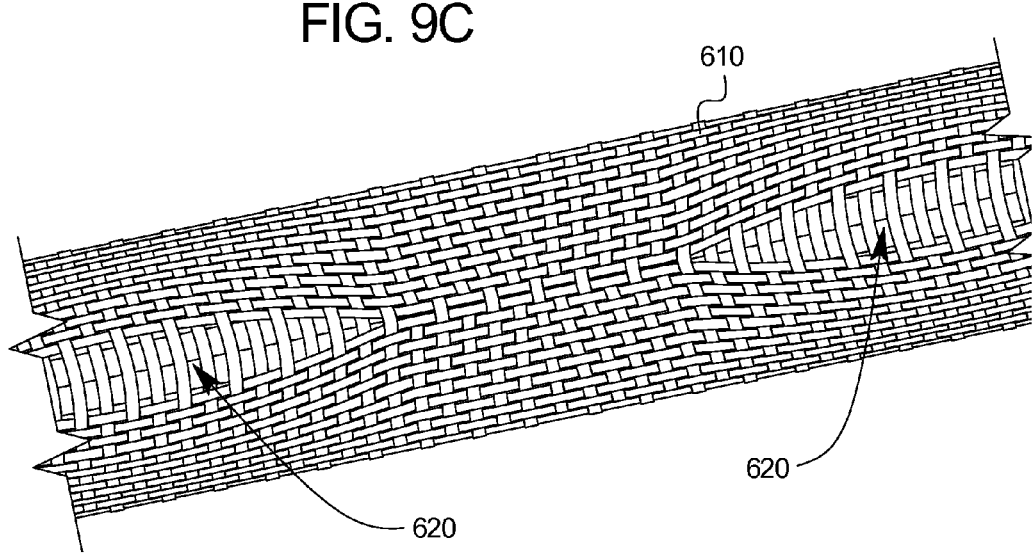
FIG. 9C is a schematic illustration of a textile sleeve after a weft thread has been moved away from the remainder of the textile sleeve.

FIG. 9C illustrates the example textile sleeve 610 after multiple weft threads have been engaged and moved away from the remainder of the textile sleeve 610 through repetition of steps 512 and 514. A longitudinal gap 620 has formed as a result of the movement.

Figure 9D:
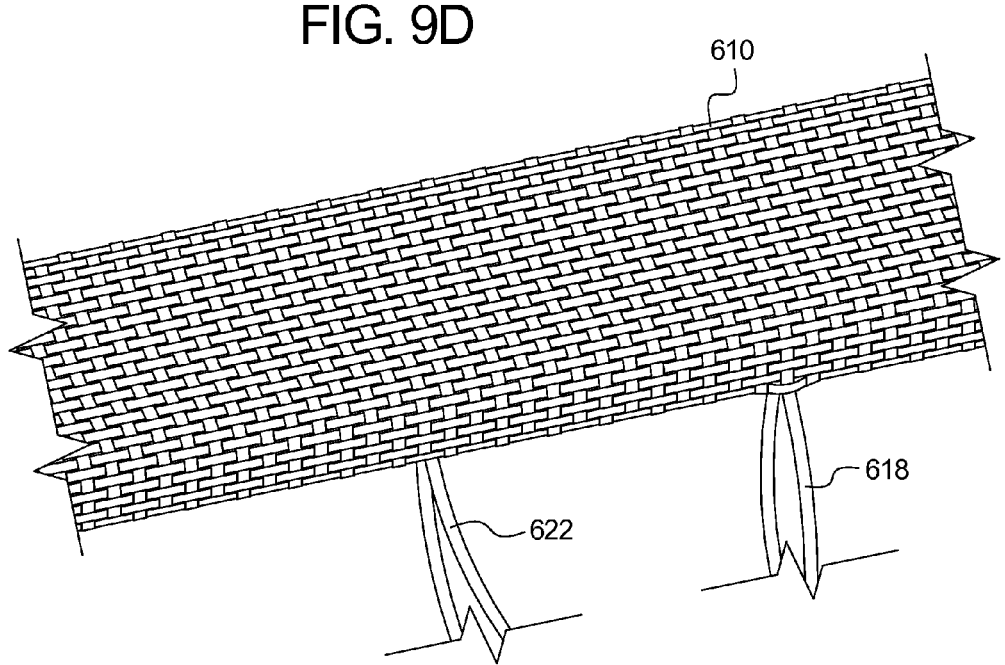
FIG. 9D is a schematic illustration of a textile sleeve after formation of two extended weft loops.

FIG. 9D illustrates the example textile sleeve 610 after the optional step 516 or manipulating the textile sleeve 610 to remove the longitudinal gap has been performed. Multiple extended weft loops 618, 622 are present as a result of engaging and moving multiple weft threads, and the longitudinal gap has been removed.

Another step 518 comprises manipulating one or more extended weft loops. This step can be performed to place the extended weft loop(s) in a suitable configuration for the step 520 of securing the textile sleeve to the balloon, described below. Any suitable technique can be used to perform this step, and a skilled artisan will be able to select an appropriate technique based on various considerations, including any desired final structure for the balloon catheter being made, such as the example structures described herein, and any general or localized strength considerations of the balloon catheter being made. Examples of suitable techniques for performing this step 518 include cutting the extended weft loop(s) to create free ends of the weft thread that can be knotted to each other or secured to the balloon as free ends, wrapping the extending weft loop(s) around a portion or portions of the textile sleeve to form a wrapped extended weft loop(s) that can be secured to the balloon, and weaving the extended weft loop(s), or one, at least one, or both of the free ends, back into the textile sleeve. Also, any suitable combination of these and/or other techniques can be used when manipulating multiple extended weft loops in a particular method. Indeed, as described above, it may be desirable to use different techniques to produce a catheter having different structure resulting from manipulation of extended weft loops at different locations on the balloon/textile sleeve portion of the catheter.

While the step 518 of manipulating one or more extended weft loops can be performed to place the extended weft loop(s) in a suitable configuration for the step 520 of securing the textile sleeve to the balloon, no specific order of these two steps is required. The step 518 can be performed prior to, during, or after step 520 is performed. For example, the step 518 can be performed by wrapping extending weft loop(s) around a portion or portions of the textile sleeve to form a wrapped extended weft loop(s). Step 520 can then be performed to secure the textile sleeve to the balloon, such as by fusing the textile sleeve to the balloon. In another example, step 520 can be performed to secure the textile sleeve to the balloon, such as by applying a suitable coating to the textile sleeve and balloon assembly. As the coating is setting, or after it has set, step 518 can be performed, such as by cutting the extended weft loop(s) to create free ends of the weft thread that can then be knotted to each other, left as free ends, or further secured to the balloon.

While embodiments described herein include knotted free ends within the body portion of the textile sleeve that are secured to the body portion of the balloon, it is noted that free ends of a weft thread can be left in the body portion without forming a knot using the free ends in this portion of the textile sleeve. The inventors believe that the use of knots in the body portion is desirable, but not necessary.

Another step 520 comprises securing the textile sleeve to a balloon usable in a balloon catheter. Any suitable technique can be used for performing this step, and a skilled artisan will be able to select an appropriate technique for a particular method based on various considerations, including the nature of the material of the balloon and of the textile sleeve. Examples of suitable techniques include placing the balloon or a balloon precursor within the interior chamber of the textile sleeve and heating the balloon or balloon precursor and textile sleeve to fuse the elements together. If a balloon precursor is used, it can be inflated as part of this step as well. Another example includes applying an adhesive to the balloon or a balloon precursor and/or the textile sleeve to adhere the balloon or balloon precursor and textile sleeve elements to each other. Also, the balloon or a balloon precursor can be attached to a catheter prior to performance of this step such that performance of this step completes the making of a balloon catheter, or the balloon or a balloon precursor can be separate from an elongate member of a catheter such that another step of securing the balloon or a balloon precursor and the textile sleeve secured to it to an elongate member of a catheter such that a balloon catheter is produced can be included.

Examples of suitable techniques for securing the textile sleeve to a balloon can be found in United States Patent Application Publication No. 20110046654 for TEXTILE-REINFORCED HIGH-PRESSURE BALLOON (Kuppurathanam, inventor) and in United States Patent Application Publication No. 20130261547 for METHOD OF MAKING A MEDICAL BALLOON (Cook Medical Technologies, Applicant). The disclosure of each of these published applications is hereby incorporated into this disclosure for the purpose of describing suitable techniques for securing a textile sleeve to a balloon.

Figure 10:
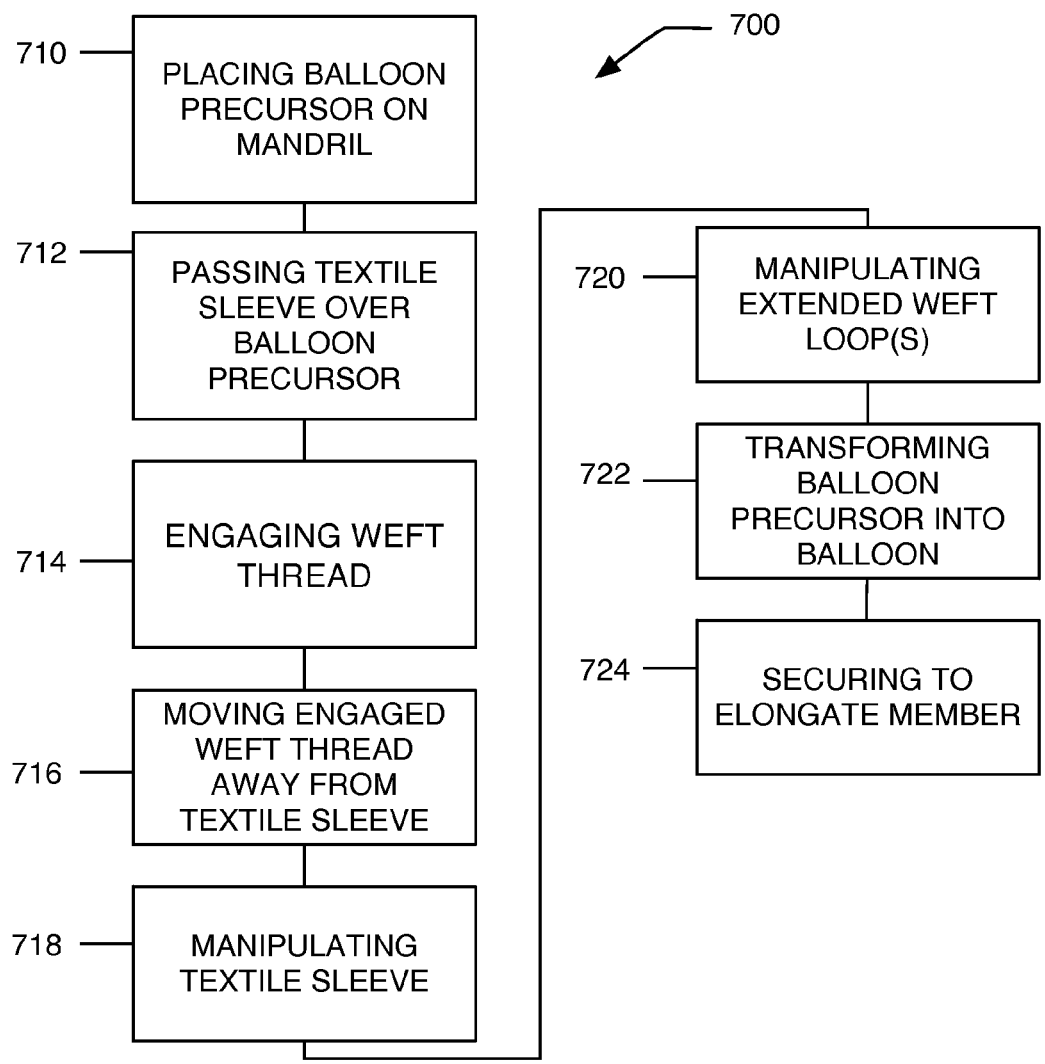
FIG. 10 is a flowchart representation of an example method of making a catheter.

FIG. 10 is a flowchart representation of another example method 700 of making a catheter.

An initial step 710 of the method 700 comprises placing a balloon precursor on a mandril. The balloon precursor can be a parison suitable for use in a blow molding process to form a final balloon shape.

Another step 712 comprises passing a textile sleeve over the balloon precursor such that the balloon precursor is disposed within the interior cavity defined by the textile sleeve. The textile sleeve can comprise any suitable textile sleeve, including those described herein. Also, the mandril can comprise any suitable mandril, including a metal rod, a plastic rod, and an elongate member that is a component of a catheter or a precursor of a component of a catheter.

Another step 714 comprises engaging a weft thread of the textile sleeve with a tool. Any suitable tool can be used to perform this step, including a finger or fingers, a needle and any other suitable tool. Furthermore, any suitable technique for engaging a weft thread with a tool can be used, and the technique need only result in making contact between the tool and the weft thread that enables the moving step 716 described below. For example, if the tool comprises a needle, this step 714 can be accomplished by placing the needle between a selected weft thread and other weft and warp threads such that the moving step 716 can be performed. It is believed to be advantageous to perform this step 714 by engaging only a single weft thread.

Another step 716 comprises moving the engaged weft thread away from the remainder of the textile sleeve to form an extended weft loop. This step can be performed in any suitable manner. For example, a force can be applied to the tool used in the engaging step 714 to cause it to move away from the textile sleeve and mandril such that an extended weft loop is formed. This step 716 can be performed to any suitable degree, typically measured by the size of the extended weft loop or the ability to continue moving the engaged weft thread away from the textile sleeve and the mandril. The inventors have determined that it is suitable to continue the moving of this step 716 until the textile sleeve is "necked down" onto the balloon precursor such that the textile sleeve is secured to the balloon precursor at the point at which the extended weft loop has been formed. This secures these elements together at this point but leaves the balloon precursor free of the textile sleeve at other points, such as within the cavity of the textile sleeve. Also, if it is desirable in a particular method to have loose ends formed in the extended weft loop, such as in the example catheters described above, the inventors have determined that it is suitable to continue this moving step 716, if possible, until the engaged weft thread breaks and the loose ends are formed.

If it is desirable and/or necessary to produce multiple extended weft loops, the step 714 of engaging a weft thread and the step 716 of moving the engaged weft thread away from the textile sleeve can be repeated a desired number of times, engaging a different weft thread or a different portion of a weft thread with each performance of the steps 714, 716 to produce a desired number of extended weft loops.

The step 716 of moving the engaged weft thread away from the remainder of the textile sleeve can produce a longitudinal gap in the textile sleeve as the extended weft loop or extended weft loops are formed. If the presence of a longitudinal gap is undesirable in the catheter being made, an optional step 718 or manipulating the textile sleeve to remove the longitudinal gap can be performed. If included, this step 718 can be performed using any suitable technique. A skilled artisan will be able to select a suitable technique for a particular method based on various considerations, including the nature of the material or materials of the textile sleeve. The inventors have determined that a simple digital manipulation of the warp and/or weft threads of the textile sleeve near and/or around the longitudinal gap is typically sufficient to remove a longitudinal gap or reduce a longitudinal gap to an acceptable size, configuration, and/or orientation.

Another step 720 comprises manipulating one or more extended weft loops. This step can be performed to place the extended weft loop(s) in a suitable configuration for the step 722 of securing the textile sleeve to the balloon, described below. Any suitable technique can be used to perform this step, and a skilled artisan will be able to select an appropriate technique based on various considerations, including any desired final structure for the balloon catheter being made, such as the example structures described herein, and any general or localized strength considerations of the balloon catheter being made. Examples of suitable techniques for performing this step 720 include cutting the extended weft loop(s) to create free ends of the weft thread that can be knotted to each other or secured to the balloon as free ends, wrapping the extending weft loop(s) around a portion or portions of the textile sleeve to form a wrapped extended weft loop(s) that can be secured to the balloon, and weaving the extended weft loop(s), or one, at least one, or both of the free ends, back into the textile sleeve. Also, any suitable combination of these and/or other techniques can be used when manipulating multiple extended weft loops in a particular method. Indeed, as described above, it may be desirable to use different techniques to produce a catheter having different structure resulting from manipulation of extended weft loops at different locations on the balloon/textile sleeve portion of the catheter.

While the step 720 of manipulating one or more extended weft loops can be performed to place the extended weft loop(s) in a suitable configuration for the step 724 of securing the textile sleeve to the balloon, no specific order of these two steps is required. The step 720 can be performed prior to, during, or after step 724 is performed. For example, the step 720 can be performed by wrapping extending weft loop(s) around a portion or portions of the textile sleeve to form a wrapped extended weft loop(s). Step 724 can then be performed to secure the textile sleeve to the balloon, such as by fusing the textile sleeve to the balloon. In another example, step 724 can be performed to secure the textile sleeve to the balloon, such as by applying a suitable coating to the textile sleeve and balloon assembly. As the coating is setting, or after it has set, step 720 can be performed, such as by cutting the extended weft loop(s) to create free ends of the weft thread that can then be knotted to each other, left as free ends, or further secured to the balloon.

While embodiments described herein include knotted free ends within the body portion of the textile sleeve that are secured to the body portion of the balloon, it is noted that free ends of a weft thread can be left in the body portion without forming a knot using the free ends in this portion of the textile sleeve. The inventors believe that the use of knots in the body portion is desirable, but not necessary.

Another step 722 comprises transforming the balloon precursor into a balloon suitable for use in a balloon catheter. Any suitable technique can be used for performing this step, and a skilled artisan will be able to select an appropriate technique for a particular method based on various considerations, including the nature of the material of the balloon precursor. Examples of suitable techniques include placing the assembly of the balloon precursor and textile sleeve into a cavity of a blow mold and then inflating the balloon precursor in a blow molding process, effectively forming the balloon and forcing the material of the balloon precursor into direct contact with the textile sleeve during the molding process.

Another step 724 comprises securing the textile sleeve to the balloon. This step 724 can be accomplished using any suitable technique, process and materials. Furthermore, this step 724 can be performed during or subsequent to the performance of step 722. For example, the use of adhesives and/or the application of heat during performance of step 722 can facilitate the securement of the textile sleeve to the balloon as it is being formed from the balloon precursor.

The balloon precursor can be attached to a catheter prior to performance of the method step such that performance step 724 completes the making of a balloon catheter, or the balloon precursor can be separate from an elongate member of a catheter such that another step 726 of securing either the balloon precursor, balloon precursor and textile sleeve assembly, or the balloon and textile sleeve assembly to an elongate member of a catheter such that a balloon catheter is produced can be included. Those with ordinary skill in the art will appreciate that various modifications and alternatives for the described and illustrated embodiments can be developed in light of the overall teachings of the disclosure. Accordingly, the particular structures and methods disclosed are intended to be illustrative only and not limiting as to the scope of the invention, which is to be given the full breadth of the claims and any and all equivalents thereof.

I claim:

1. A method of making a catheter, comprising:
    placing a textile sleeve having a plurality of warp threads and at least one weft thread on a mandril;
    engaging a weft thread of the textile sleeve with a tool;
    moving the engaged weft thread away from the remainder of the textile sleeve to form an extended weft loop;
    manipulating the extended weft loop;
    securing the textile sleeve to a balloon; and
    securing the balloon to an elongate member defining a lumen such that movement of fluid through the lumen moves the balloon between inflated an uninflated configurations.

2. The method of claim 1, wherein the step of manipulating the extended weft loop comprises cutting the extended weft loop to create free ends of the weft thread.

3. The method of claim 2, further comprising knotting the free ends to each other.

4. The method of claim 2, further comprising securing the free ends to the balloon.

5. The method of claim 2, further comprising weaving at least one of the free ends into the textile sleeve.

6. The method of claim 1, wherein the step of manipulating the extended weft loop comprises wrapping the extending weft loop around a portion of the textile sleeve.

7. The method of claim 6, further comprising securing the extended weft loop to the textile sleeve.

8. The method of claim 1, wherein the step of manipulating the extended weft loop comprises weaving the extended weft loop into the textile sleeve.

9. The method of claim 1, wherein the steps of engaging a weft thread and moving the engaged weft thread are repeated to create a second extended weft loop.

10. The method of claim 1, wherein the steps of engaging a weft thread and moving the engaged weft thread are repeated multiple times to create multiple extended weft loops.

11. The method of claim 1, wherein the step of securing the textile sleeve to a balloon comprises fusing the textile sleeve and a balloon together.

12. The method of claim 1, wherein the step of securing the textile sleeve to a balloon comprises using an adhesive to adhere the textile sleeve and a balloon to each other.

13. The method of claim 1, wherein the step of manipulating the extended weft loop is performed prior to the step of securing the textile sleeve to a balloon.

14. The method of claim 1, wherein the step of manipulating the extended weft loop is performed after the step of securing the textile sleeve to a balloon.

15. The method of claim 1, wherein the steps of manipulating the extended weft loop and securing the textile sleeve to a balloon are performed contemporaneously.

16. A method of making a catheter, comprising:
    moving a weft thread away from the remainder of a textile sleeve comprising the weft thread and at least one warp thread to form an extended weft loop;
    manipulating the extended weft loop;
    securing the textile sleeve to a balloon precursor;
    transforming the balloon precursor into a balloon suitable for use in said catheter; and
    securing the balloon to an elongate member defining a lumen such that movement of fluid through the lumen moves the balloon between inflated an uninflated configurations.

* * * * *